United States Patent [19]

Feldman

[11] 4,354,843
[45] Oct. 19, 1982

[54] SPACIAL ORIENTATION INSTRUCTION DEVICE

[76] Inventor: Brian Feldman, 338 E. 22nd St., Apt. 2C, New York, N.Y. 10010

[21] Appl. No.: 36,183

[22] Filed: May 4, 1979

[51] Int. Cl.³ .............................................. G09B 19/00
[52] U.S. Cl. ..................................... 434/236; 434/322
[58] Field of Search ...................... 35/6, 9 B, 14, 22 R, 35/31 C; 273/265, 237; 340/717, 311, 330; 434/236, 322

[56] References Cited

U.S. PATENT DOCUMENTS

| | | | |
|---|---|---|---|
| 2,870,549 | 1/1959 | Craine | 35/22 R |
| 3,149,841 | 9/1964 | Hullman | 340/378.3 |
| 3,346,968 | 10/1967 | Dellinger | 35/6 |
| 3,526,971 | 9/1970 | Shipley | 35/22 R |
| 3,543,418 | 12/1970 | Press | 35/22 R |
| 3,751,825 | 8/1973 | Barrett | 35/6 |

*Primary Examiner*—David R. Sadowski
*Attorney, Agent, or Firm*—Bauer & Amer

[57] ABSTRACT

A light display in which the individual lights are positioned in relation to an x and y axis, and in which further any one selected light is operated in tandem, either automatically or manually by an instructor resulting in the illumination thereof, and then by the patient, usually a child, resulting in the turning off of the light. The operational control over the selected light, as just generally noted, is achieved using correspondingly x and y axis-positioned buttons, thus requiring the patient to determine the corresponding position of the position-related light and button involved, with the result that the patient receives spacial orientation instruction.

1 Claim, 8 Drawing Figures

SPACIAL ORIENTATION INSTRUCTION DEVICE

The present invention relates generally to a device for effectively providing spacial orientation instruction to a patient, usually a child, suffering from a disorder that inhibits proper perception of directional concepts, i.e. discerning "left" from "right", "up" from "down", estimating distances, etc., and more particularly to improvements in the functioning and operational mode of such instructing devices that significantly enhance their effectiveness.

As understood, children who have perceptual motor dysfunctions, i.e. a disorder referred to by many, or in any event often likened to, dyslexia, can be assisted to overcome this disorder by being trained, or instructed, in distinguishing "left" from "right", "up" from "down", and otherwise being made to perceive directional concepts. These children, upon being effectively instructed as just generally noted, would be able to project the learned directional concepts in the performance of everyday type chores. Heretofore, however, there has been only nominal success in alleviating the above noted disorder in children particularly, by way of training and instruction.

Underlying the present invention is the recognition that the imparting of special orientation instruction is often undermined, not by any condition in the patient related to the disorientation disorder, but by the short attention span, lack of motivation, and other such unfavorable conditions of attitude or receptiveness of the patient. Stated another way, the within invention recognizes that for instruction to be effectively imparted to children, particularly involving spacial orientation, that the instructing device should have "play value", in much the same way that an effective toy must have this characterizing feature.

Broadly, it is an object of the present invention to provide an improved spacial orientation instruction device, suited particularly for use with dyslexic children, overcoming the foregoing and other shortcomings of the prior art. Specifically, it is an object to provide an instructing device, as just generally noted, that contemplates in its operational mode a light display and manipulation of the individual lights thereof in such manner as to be appealing, and thus have "play value", for children, to thereby provide motivation for their active participation in an instruction session using the said device.

A spacial orientation instruction device demonstrating objects and advantages of the present invention includes, in a preferred embodiment, a light display consisting of six horizontally and vertically oriented rows of lights. Associated therewith are plural indicia-bearing slides mounted in positions to be illuminated by the lights. Also provided are light-operating switches for selectively illuminating a selected one of the slides and, for the patient (i.e. child) a button control having the same six horizontally and vertically oriented rows of buttons, each such button being operatively effective to terminate the continued illumination of any slide incident to the child actuating the particular button that is in a location corresponding to the illuminated slide. As a consequence, selecting an illumination-terminating button contributes to providing recognition of the spacial orientation of the location of the illuminated slide and, most important, the child is motivated to search for and find the proper button, as if playing a game.

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein.

Figure 1:
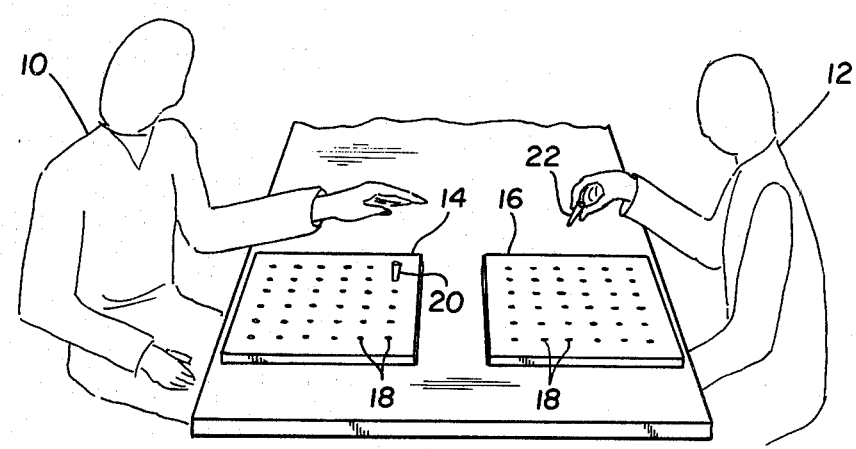
FIG. 1 is a perspective view illustrating typical prior art equipment and a method of using same for providing instruction in spacial orientation to children or older patients suffering from disorders affecting directionality, laterality, orientation, etc.

As understood, there are many individuals, and particularly children, who have a disorder of the brain circuitry which is manifested by symptoms such as letter reversals, mirror writing and difficulty in distinguishing "left" from "right". The disorder is a form of dyslexia and is believed to afflict from 2% to 5% of school children who are otherwise normal and have average or superior intelligence. While there is no consensus on what gives rise to the disorder, some doctors believing it to be due to a faulty connection somewhere between the brain and the inner ear, while others believing it to actually involve some form of brain damage, albeit of a minimal nature, there is a consensus in the understanding that with proper instruction a patient suffering from the disorder mentioned can improve his spacial orientation and thus effectively overcome the problems to which it gives rise. Thus, as is illustrated in FIG. 1, there is currently wide use of instruction sessions involving a qualified therapist 10 and patient 12 and a cooperating pair of pegboards 14 and 16, each with a similar arrangement of horizontally and vertically oriented peg-openings, individually and collectively designated 18. The spacial orientation instruction that is intended to be provided the patient 12 according to the prior art technique of FIG. 1 involves the placement of a peg 20 by the instructor 10 in a selected opening 18, such placement being observed by the patient 12, who is seated across from the instructor 10. Patient 12 is then required to select the same peg opening 18 which occupies the same position in his pegboard 16 that corresponds to the position occupied by peg 20 in the instructor's board 14. As may be readily surmised, the mental process imposed on the patient 12 to achieve this objective requires distinguishing between his "right" and "left", as well as between the directions "up" and "down", and counting in these two directions the appropriate number of positions as denoted by the openings 18 so as to eventually permit the selection of that specific opening 18 for the placement of the patient's peg 22 that will provide the corresponding position in board 16 that duplicates the peg positioning provided by the instructor 10 in board 14.

As already noted, the mental process or reasoning required of the patient 12 as just noted is effective in improving the spacial orientation of the patient. However, a most serious shortcoming of the prior art procedure of FIG. 1, that is particularly aggravated or acute if the patient 12 is a young child, which is often the case, is that the span of attention, mental alertness and other related aspects of the mental state of such a patient are lacking in order to enable such patient to effectively participate in the instructor-duplicating procedure of FIG. 1. Stated another way, a dyslexic child typically finds the prior art procedure of FIG. 1, as just generally described, too boring and otherwise unappealing to want to actively participate in such procedure, and for this reason thus fails to receive the full benefit of any spacial orientation instruction that is forthcoming during any prolonged period of time.

Underlying the present invention is the recognition that an effective spacial orientation instruction device, having due regard for its use to a significant extent with children, must have as part of its operational mode an aspect which can be most aptly characterized as "play value". That is, the device by its functioning must appeal to a young patient and as such produce a corresponding motivation to participate in the instruction session utilizing the device. Such a device, in accordance with the present invention, is illustrated in FIGS. 2-7, and exemplary electrical circuits for same in FIG. 8. In clinical testing, the device, generally designated 30, has been effective in only six months in dramatically teaching a ten year old, having the previously referred to perceptual motor dysfunctions, to discern his "left" from his "right", "up" from "down", and to otherwise effectively project directional concepts. This result, which has been duplicated by dramatically improved performance with many other children having perceptual motor dysfunctions is believed, to a large extent, to be due to the use and the embodiment in the functioning of the device 30 of a light display, sound signals and buttons which require actuation, all to the end of imparting a "game-like" concept in the operation thereof. The aforesaid contributes to initially obtaining and thereafter maintaining the attention of the patient directed toward participating fully in the instruction session utilizing the device 30.

Figure 3:
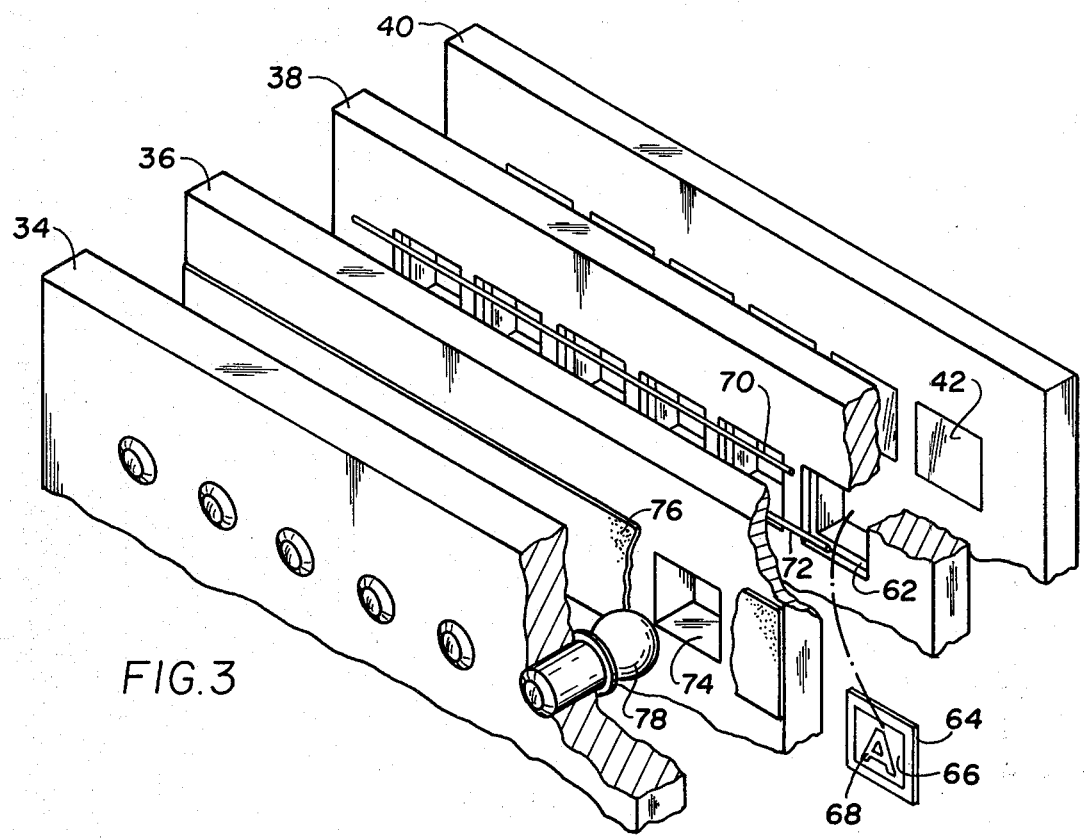
FIG. 3 is a partial exploded view showing the cooperative arrangements of components disposed internally of the housing of the device of FIG. 2, and wherein portions of the components are broken away to better illustrate details of the structural features thereof; j
Figure 4:
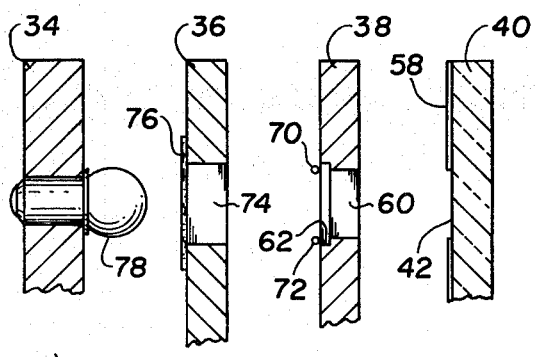
FIG. 4 is a sectioned side elevational view projected from FIG. 3, showing further structural details.
Figure 5:
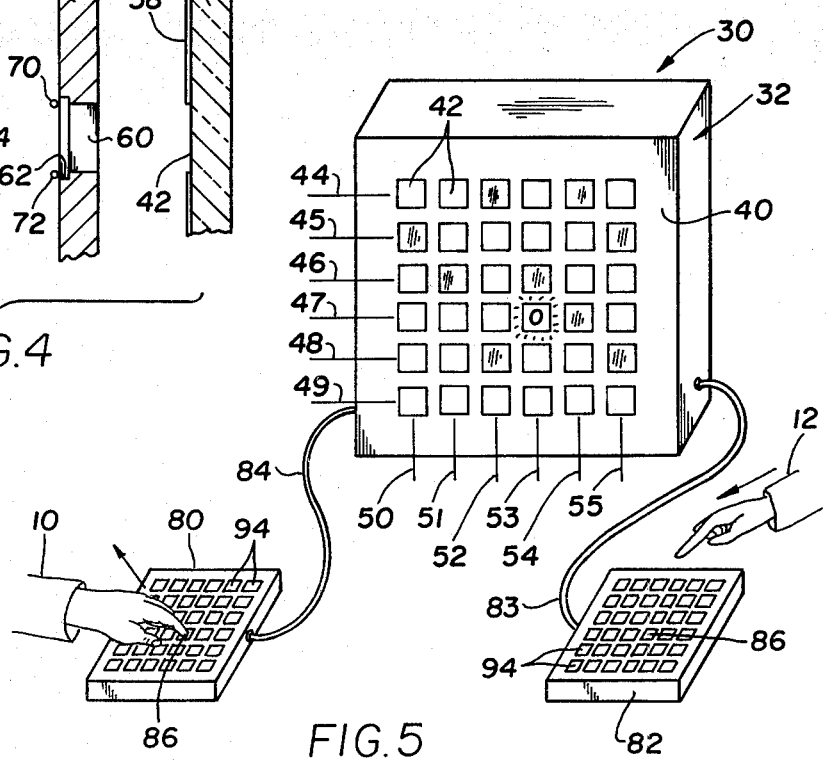
FIG. 5 is a perspective view illustrating a typical instruction session using the within improved device.

In a preferred embodiment, device 30 includes an external housing 32 in which, as best illustrated in FIGS. 3, 4, there is appropriately disposed four vertically oriented spaced apart panels 34, 36, 38 and 40, the last named panel 40 serving as the front of the housing 32. Starting with panel 40, the same will be understood to be preferably of a transparent plastic construction material on which there has been effectively delineated an arrangement of 36 windows, individually and collectively designated 42. The arrangement more particularly is one that consists of six vertically oriented and six horizontally oriented rows wherein the position of each window 42 is at the intersection therebetween. To illustrate this arrangement there has been applied to FIG. 5 horizontally and vertically oriented reference lines, the former designated 44-49 to respectively identify the six horizontal rows, and the vertically oriented lines designated 50-56 to identify the six vertical rows. To delineate the appropriate square or rectangular shape for each window 42, panel 40, as best illustrated in FIG. 4, is provided with an opaque covering on its rear surface, designated 58, over all but the areas allotted for the windows 42. That is, the transparency of the plastic panel 40 exists only in the window area 42 and is effectively masked by the opaque paint or surface 58 applied over the remaining surface area of the rear surface of panel 40.

Panel 38 situated immediately behind panel 40 is appropriately machined in each location that is horizontally aligned with a window 42 of panel 40 with a counterbore opening 60. The counterbore provides a shoulder 62 for effectively seating a photographic slide 64 which, on its projection surface 66 presents for projection indicia such as letters, as exemplified by letter "A" designated 68 in FIG. 3. In lieu of letters, the slide 64 can present numbers for projection or even shapes and objects that have meaning to a child who will be instructed using the device 30. Any effective retaining means may be used to hold each slide 64 in its cooperating compartment 62, one such preferred means being elastomeric strings 70 and 72 attached in spanning relation along each horizontal row in a strategic position behind the rows of the openings 60 of panel 38.

The light that is used to individually illuminate a selected slide 64 is beamed through panel 36, and thus this panel has an opening 74 in each location aligning with previously noted aligned structural features 60 and 42. To effectively diffuse the slide-illuminating light, and thus obviate any annoying glare, any appropriate means may be employed. A simple and preferred means is a strip of light-diffusing paper 76, such as tissue, positioned horizontally across the rear of the rows of openings 74.

The final or rearwardly disposed panel 34, as clearly illustrated in the drawings, mounts an electrically energized bulb 78 for each window 42 in effective slide-illuminating position rearwardly of each cooperating slide 64. The thirty-six bulbs 78 are appropriately electrically connected to a power source, which may be ordinary line current or a battery, so as to be selectively illuminated and, in turn, will correspondingly illuminate a cooperating slide 64 so that the indicia 68 of the slide is readily visible to, and thus readily perceived by, a child in facing relation to the light display board 40. In this connection, it should be noted by inspection of both front elevational views presented by FIGS. 2 and 5 that not only is the specific window that is illuminated readily perceived by the patient, but also so are the locations of the non-illuminated windows. Thus, the patient by studying the display consisting of the non-illuminated window locations as well as the specific location therein that is illuminated can effectively determine, using the required mental process or reasoning to do so, what specific location, denoted by the intersection of a specific horizontal and by a specific vertical row at what corresponding specific location an illuminated indicia is being presented. For completeness' sake, it is noted in FIG. 5 that the letter "O" is illuminated in the window which is at the intersection of horizontal row 47 and vertical row 53. More important, at least from the mental reasoning imposed on the patient reading the illuminated letter "O", the position thereof is four rows from his "left" and four rows down from the "top". This interpolation of the position of the illuminated letter "O" should be readily recognized as involving, and therefore teaching the child, directional concepts. On the basis of this instruction, the child in turn then projects these directional concepts in the performance of everyday type chores such as reading, writing and learning to follow directions in space.

To operate the light display that is perceived in panel 40, use is made of a button control 80 for the instructor and a similarly constituted and constructed button control 82 for the patient. In both controls 80 and 82, it is contemplated that actuation of the buttons thereon will effect the light display of panel 40; such effect, however, will be in a correspondingly opposing relation. That is, the depressing of a button of control 80 will cause illumination of a specific window 42 of panel 40, whereas the depressing of only the "correct" button of control 82 by the patient will terminate that illumination, while the depressing of any other button will be without any significant effect. To achieve this cooperating interacting between the controls 80 and 82, they are each electrically connected by conduits 84 and 83 to the lights 78 via any appropriate circuit, one such preferred and effective conduit being shown in FIG. 8. The FIG. 8 circuit, which it will be understood is provided to control the illumination and termination thereof in each light 78, is operated by a corresponding pair of buttons in the controls 80 and 82, such buttons being the two buttons in each control that occupy the same position as the light they control.

Figure 8:
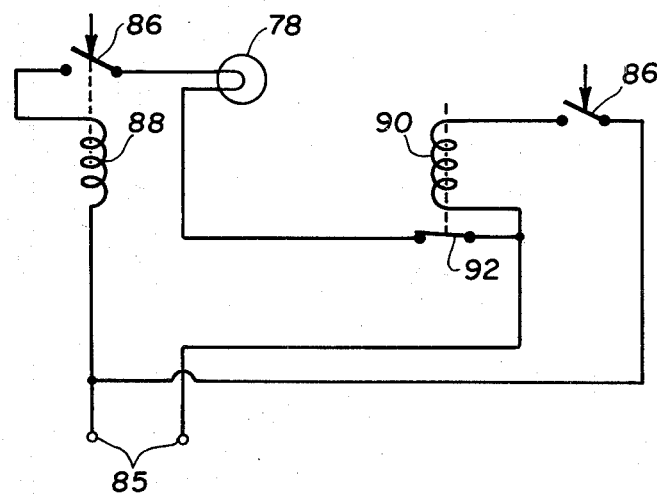
FIG. 8 is a simplified exemplary circuit diagram for operating the lights and other electrical components of the within device in a manual mode.

Referring now to FIG. 8, the circuit includes a connection 85 to an appropriate power supply. The instructor, by depressing a selected button on his control, as represented by the open switch 86, effectively completes the circuit for the light or bulb 78 position associated with that switch. This, in turn, results in the energizing of the solenoid coil 88 which it will be understood holds switch 86 closed even after the instructor releases the manual pressure which initially closed the switch. As already noted, for the patient to provide a "proper" response to the visual display presented on panel 40, he is required to depress the button in his control 82 that occupies the same position as the button depressed by the instructor in the instructor's control 80. Assuming the patient does so, and to show its positional relation to the button selected by the instructor the same is also designated 86, it will be understood to result in the closing of a normally open switch associated therewith, as illustrated in FIG. 8. The closing of button or switch 86 thus results in the completion of a circuit to the power supply 85 which includes the solenoid coil 90 and the energizing of this coil which, in turn, results in the opening of normally closed switch 92. Since switch 92 is included in the circuit for light 78, the opening of this switch thus disconnects light 78 from the power supply 85 and results in the termination of the energization of the light 78. When light 78 is turned off, this terminates the illumination of the window in the light display panel 40 and indicates a "correct" response by the patient. Further auditory positive reinforcement may be provided by a buzzer which is momentarily actuated upon condition of a "correct" response.

It is convenient at this point in the description to note that in lieu of having a manual input into the device 30 by an instructor actually present and actuating a selected button or switch 86, that device 30 can also be provided with an effective computer-type program which, in a well understood manner, will cause the illumination of selected windows 42 in successive random fashion. In this operational mode each successively illuminated window will first require that there be a "proper" response by the patient 12, as already described, before the next window is automatically illuminated. In addition, a counter may be incorporated to tally the number of correct responses per unit time. Thus a quantitative measure of the child's ability to encode spacial coordinates is readily available, and progress readily assessed.

In addition to play value, the automatic feature further allows the child to work at his own pace without the psychological burden of the examiner constantly present. Such operational mode also provides an assessment of the maximum number of correct responses with the limiting factor being solely the child's ability to encode and match the coordinates, i.e. it provides a direct measure not related to the supervisor's speed of action, but rather only the patient's speed of action.

For purposes of completeness, the corresponding arrangement of buttons noted in connection with each of the controls 80 and 82 will be understood not only to be identical to each other, but also identical to the locations of the windows 42 of the panel 40. In other words, the buttons, individually and collectively designated 94 in each of the controls 80 and 82, will be understood to be arranged in six horizontal and six vertical rows providing an available 36 buttons, one for each window 42 occupying the same position or location.

Further additions to the electrical circuitry as exemplified by FIG. 8 for operating the within device 30 which are not shown because they are believed to be well within the expertise of those versed in the art, include a counter for counting each "correct" response of the patient during a typical instruction session. Also, in addition to terminating the illumination of the window, the device 30, as already noted, may also include a bell or other sound device to further indicate a "correct" response by the patient, such sound signal further contributing to the positive reinforcement and "play value" of the within device.

Figure 2:
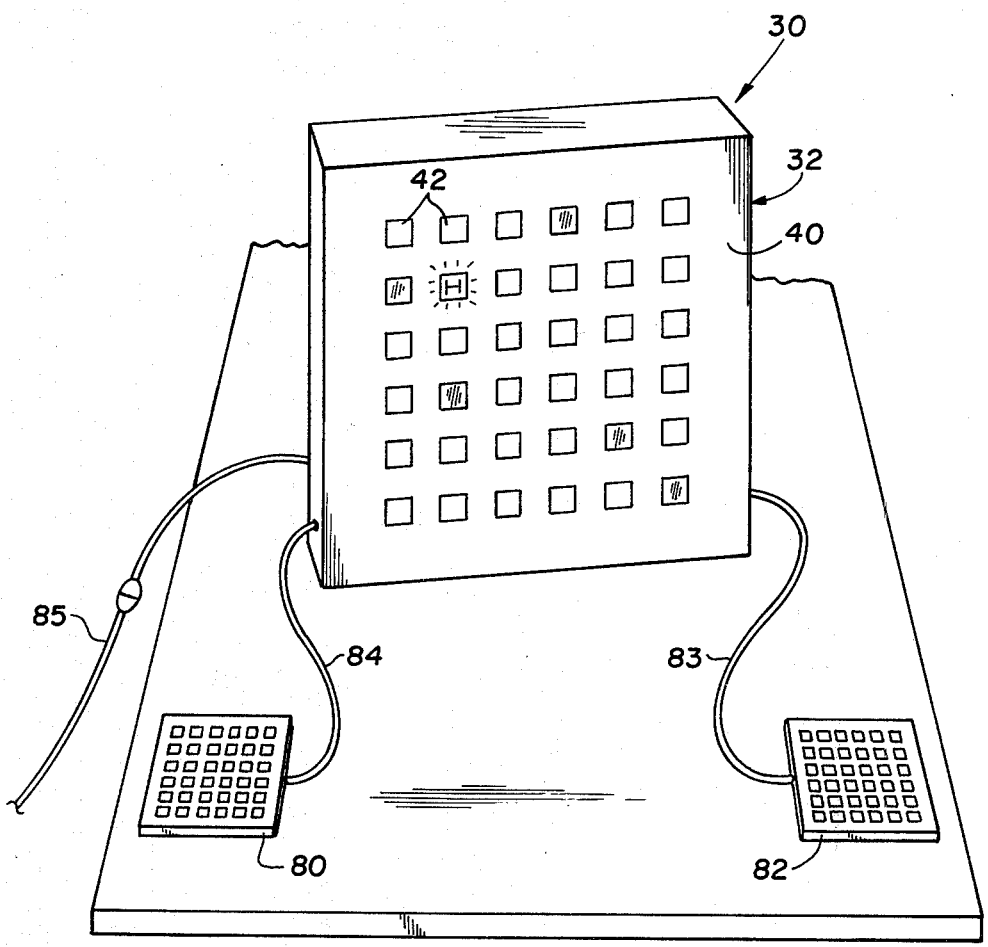
FIG. 2 is a perspective view of a device also for providing spacial orientation instruction, but in an improved and more effective manner in accordance with the present invention.
Figure 6:
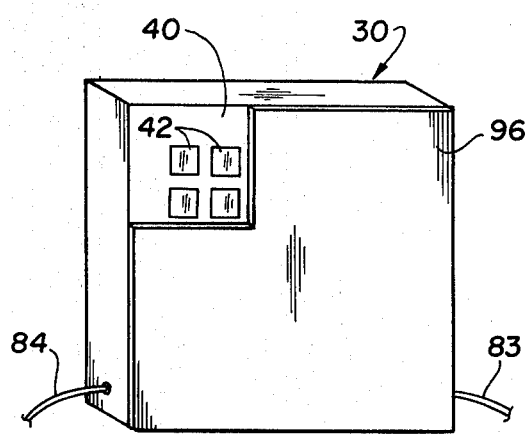
FIGS. 6 and 7 are both front perspective views illustrating contemplated set-ups of the within device in accordance with successive increases in the levels of complexity in relation to the spacial orientation instruction provided by said device.
Figure 7:
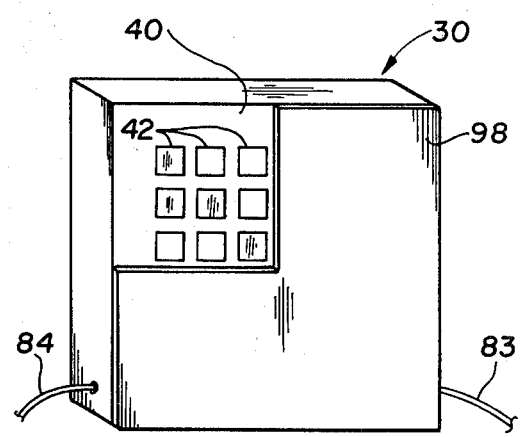

Reference should now be made to FIGS. 6 and 7 which illustrate use of masking panels 96 and 98, respectively, for the front display panel 40, the purpose of which is to provide selected levels of complexity in the light display used in the instruction of the patient. In FIG. 6, for example, panel 96 masks all but four display windows 42 in the upper lefthand corner, thus greatly simplifying the determination for the patient of the position of the specific window illuminated. The next level of complexity, as illustrated in FIG. 7, is one in which all but three vertical and horizontal rows of display windows are masked. In this manner, the patient is brought in gradual steps to the point where he can effectively cope with the full six row display contemplated for the front panel 40. The complexity of the task of encoding and matching spacial coordinates can also be varied in another manner if deemed necessary. More particularly, depending upon the patient's abilities and unlike the prior art, it can also be varied. By placing the control box 82 in a vertical fashion, i.e. with the switches parallel to a frontal plane through the child, and parallel to the display unit 30. In this way, the coordinates of left/right on 30 remain as left/right on the control box 82, as do up and down. Thereafter, and only if increased complexity and increased transfer to natural environmental situations are desired, would the control box 82 be placed such that it is perpendicular to the display unit 30, as illustrated in FIG. 2. In this latter or FIG. 2 situation, left/right remains as left/right, but up/down on the display panel now corresponds to near/far on control box 82. This further aids in situations such as required in copying from blackboard to notebook, drawing, and graphing, where more complex encoding and directionality concepts are required.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. The method of providing spacial orientation instruction to a student comprising the steps of displaying to said student a plurality of display windows in an intersecting pattern of horizontally and vertically oriented rows so as to define a display location at each said intersection of said rows, successively illuminating a display window at only one said display location at a time so as to provide a corresponding single-light display to said student, and providing for actuation by said student plural buttons operatively arranged in said same pattern of horizontal and vertical rows at said display locations, each said button having a controlling operative relation over a cooperating display window having the same location in said pattern effective to terminate the illumination thereat incident to being actuated, whereby said student in the process of selecting an illumination-terminating button requires recognition of the spacial orientation of the location of said one display window selected for illumination.

* * * * *